(12) United States Patent
Ellerbrock (10) Patent No.: US 10,424,115 B2
(45) Date of Patent: Sep. 24, 2019

(54) HEAD-WORN PLATFORM FOR INTEGRATING VIRTUALITY WITH REALITY

(71) Applicant: Christof Ellerbrock, Ingelheim (DE)

(72) Inventor: Christof Ellerbrock, Ingelheim (DE)

( * ) Notice: Subject to any disclaimer, the term of this patent is extended or adjusted under 35 U.S.C. 154(b) by 0 days.

(21) Appl. No.: 14/693,336

(22) Filed: Apr. 22, 2015

(65) Prior Publication Data
US 2015/0310668 A1    Oct. 29, 2015

(30) Foreign Application Priority Data
Apr. 24, 2014    (DE) .................. 10 2014 207 749

(51) Int. Cl.
| | | |
|---|---|---|
| *G02B 27/01* | (2006.01) | |
| *G06T 19/00* | (2011.01) | |
| *H04N 5/32* | (2006.01) | |
| *A61C 9/00* | (2006.01) | |
| *A61C 1/08* | (2006.01) | |
| *A61B 90/00* | (2016.01) | |

(52) U.S. Cl.
CPC ............ *G06T 19/006* (2013.01); *A61C 1/084* (2013.01); *A61C 9/0053* (2013.01); *G02B 27/0172* (2013.01); *H04N 5/32* (2013.01); *A61B 2090/364* (2016.02); *A61B 2090/371* (2016.02); *A61B 2090/373* (2016.02); *G02B 2027/0178* (2013.01); *G06T 2200/08* (2013.01)

(58) Field of Classification Search
CPC . A61B 2090/371; A61C 1/084; A61C 9/0053; G02B 2027/0178; G02B 27/0172; G06T 19/006; G06T 2200/08; H04N 13/0239; H04N 5/32
See application file for complete search history.

(56) References Cited

U.S. PATENT DOCUMENTS

| | | | | |
|---|---|---|---|---|
| 5,608,210 A | * | 3/1997 | Esparza ............... | A61B 5/0059 250/226 |
| 6,864,911 B1 | * | 3/2005 | Zhang .................. | G03B 35/08 348/211.1 |

(Continued)

FOREIGN PATENT DOCUMENTS

| | | |
|---|---|---|
| EP | 1 739 642 A1 | 1/2007 |
| JP | H11-128248 A | 5/1999 |

(Continued)

OTHER PUBLICATIONS

European Search Report dated Aug. 25, 2015.

*Primary Examiner* — Sing-Wai Wu
(74) *Attorney, Agent, or Firm* — Norris McLaughlin, P.A.

(57) ABSTRACT

The invention relates to a device for obtaining and processing of 3D images.

The device includes a head assembly, on which two cameras are arranged, with each camera having an associated monitor for displaying a respective image of each camera, so that the optical axes of the monitors coincide with the optical axes of the eyes of a user of the device or can be aligned at least parallel to the optical axes of the eyes of a user. The device further includes a data processing unit for data processing of camera images. The device is characterized in that the cameras are synchronized with each other so that they focus on a common point with same aperture and the same zoom.

The inventive device enables 3D scanning, which is controlled by the natural vision with two eyes.

7 Claims, 11 Drawing Sheets

(56) References Cited

U.S. PATENT DOCUMENTS

| | | | |
|---|---|---|---|
| 7,367,809 B2 | 5/2008 | Takahashi | |
| 2007/0184422 A1* | 8/2007 | Takahashi | G06F 19/3437 434/262 |
| 2008/0266669 A1* | 10/2008 | Durner | G02B 27/017 359/630 |
| 2008/0319252 A1* | 12/2008 | Chapman | A61M 21/02 600/27 |
| 2009/0248184 A1 | 10/2009 | Steingart et al. | |
| 2011/0038514 A1* | 2/2011 | Weigl | A61C 13/0004 382/128 |
| 2011/0205242 A1 | 8/2011 | Friesen | |
| 2012/0056993 A1* | 3/2012 | Luqman | A61B 1/00045 348/47 |
| 2013/0050833 A1* | 2/2013 | Lewis | G06K 9/00604 359/630 |
| 2013/0172731 A1 | 7/2013 | Gole | |
| 2015/0271483 A1* | 9/2015 | Sun | H04N 17/002 348/187 |

FOREIGN PATENT DOCUMENTS

| | | |
|---|---|---|
| JP | 2001 172731 A | 8/2001 |
| JP | 2011-509812 A | 3/2011 |
| JP | 2013-034764 A | 2/2013 |
| WO | 01/05161 A1 | 1/2001 |
| WO | 03/034705 A2 | 4/2003 |
| WO | 2005/093687 A1 | 10/2005 |
| WO | 2012/075155 A2 | 6/2012 |
| WO | 2013/079437 A2 | 6/2013 |

* cited by examiner

Fig.11

HEAD-WORN PLATFORM FOR INTEGRATING VIRTUALITY WITH REALITY

TECHNICAL FIELD

The invention relates to a device for obtaining and processing of 3D images. An example of a device for obtaining and processing 3D images is an optical 3D scanner.

TECHNICAL BACKGROUND

Optical 3D scanners can be installed in enclosures that are either hand-held or supported on a tripod. Variants also exist which are installed in a free-standing enclosure.

Optical 3D scanners find industrial applications in many fields of, for example in medical technology, particularly the dental technology (dentistry). Dental 3D scanners are hereby at least partially inserted into the oral cavity. This "mouthpiece" may include, for example, a mirror or a prism for deflecting the optical axis. In some systems, this part is removable and can be sterilized. In many models, a strip light pattern is projected with this component onto the object to be scanned. The deflection of the strips is then detected by the built-in camera system.

Technical 3D scanners are based in part on the above-mentioned strip light projection technique. Frequently, the laser projection technology is used wherein a laser beam is moved over the object to be scanned and its change is detected.

Video glasses are used in the field of virtual reality. Video glasses also exist that have a built-in camera in order to switch between virtual reality and reality. It is also known to superimpose on the reality information though projection onto transparent plates, through which the user sees the reality. This technology is used, for example, in head-up displays in aircraft or motor vehicles and in the Google glass application.

SUMMARY OF THE INVENTION

According to the invention, a fresh approach to 3D scanning is selected.

For this purpose, an inventive device according to claim 1 for obtaining and processing of 3D images according to is proposed.

The invention relates to a device for obtaining and processing of 3D images. An example of a device for obtaining and processing 3D images is an optical 3D scanner.

The device includes a head assembly, on which two cameras are arranged, with each camera having an associated monitor for displaying a respective image of the associated camera, so that the optical axes of the monitors coincide with the optical axes of the eyes of a user of the device or can at least be aligned parallel to the optical axes of the eyes of a user. The device further includes a data processing unit for data processing of camera images. The device is characterized in that the cameras are synchronized with each other so as to to focus on a common spot with same aperture and the same zoom.

The inventive device enables 3D scanning, which is controlled by the natural vision with two eyes. The head assembly of the device according to the invention is placed on the head like a pair of glasses. The two cameras capture images of the object to be scanned. The image from the left camera and the right camera is displayed on the associated monitor which is arranged in front of each eye.

The novel aspect is that two camera systems are installed which mimic the function of the eye. The two camera systems are synchronized with each other, so that they can focus on a common spot. The aperture and zoom of both cameras are also synchronized.

Since both cameras take images of reality, digital information can be overlaid on the images of reality. Furthermore, thanks to the synchronized zoom, a magnified image of reality can be rendered. This magnifying function allows a wide range of new applications. Thus, the device can also be used as a microscope eyepiece when the cameras are designed for a magnification of at least 10×.

In a preferred embodiment of the device, the data processing includes superimposing digital information on the camera images.

The digital information may include 3D X-ray images of a tooth. In this case, root canals, tooth roots, nerves and/or blood vessels can be displayed.

The digital information may at least partly be imported from implant planning, in which case the data processing involves overlaying a display of a virtual implant with the camera images.

The display of the virtual implant may include a visualization of an implant axis as an extension extending beyond the virtual implant.

A surface of a new filling may be transparently overlaid.

A partial area of the surface having a height that is different from a desired height can be displayed color-coded.

The device may include at least one haptic feedback instrument and may be designed to construct with the haptic feedback instrument a virtual model.

The device may be designed to capture an optical 3D impression of the ground tooth which is then supplied to a system for computer-aided modeling and/or manufacturing.

Data may be processed on a connected computer. The computer may then also store the camera images. Alternatively or additionally, the camera images may also be displayed on one or more other monitors.

The overall system may be controlled via the data processing unit which is realized for example in the form of a connected computer.

Here, a foot switch may be connected to the computer via which the focus and/or magnification can be controlled.

Another foot switch connected to the computer may be used to control recording (storing) of single images or image sequences.

Position sensors may be included in the head assembly in order to detect the position of the eyewear.

The user may be able to switch between the left camera and the right camera as guide camera.

The two cameras may be arranged in the optical axis of the eye of the user and be individually adjustable.

Additionally or alternatively, the position of the two monitors may be adapted to the user.

Additional preferred embodiments of the invention will become apparent from the other features recited in the dependent claims.

Unless otherwise noted for a particular case, the various embodiments of the invention mentioned in this application can advantageously be combined.

Exemplary embodiments of the invention will now be described in with reference to the appended drawings, which show in an exemplary and schematic form in:

FIGS. 4-9 3D-X-ray images with superimposed with images of teeth,

Figure 1:
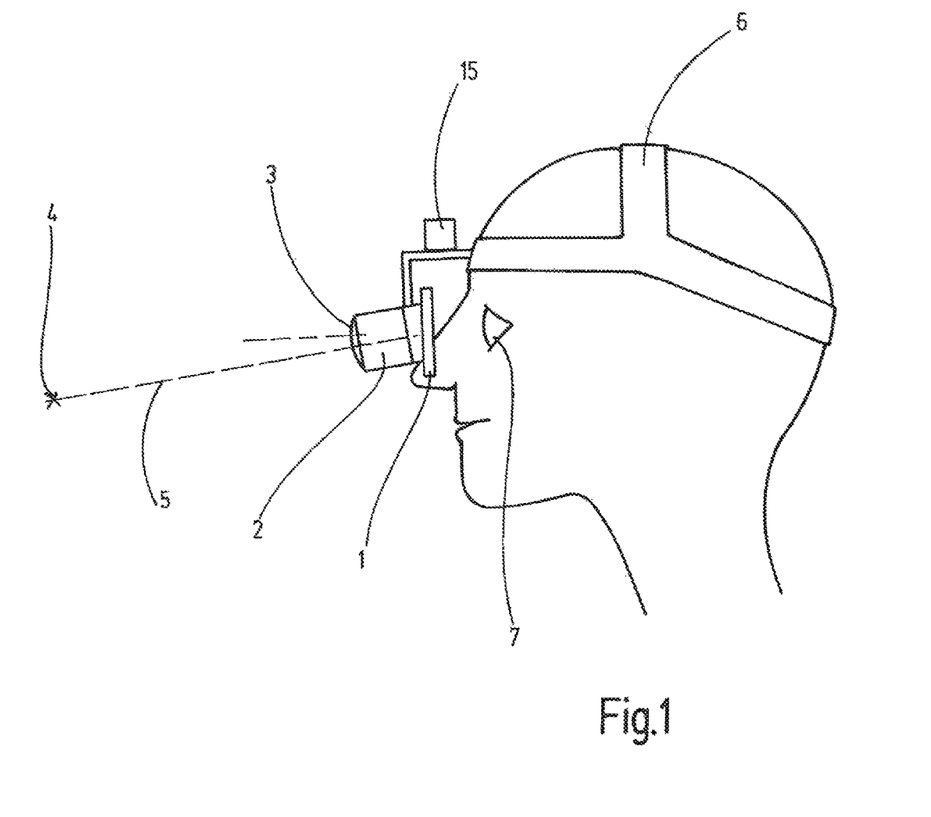
FIG. 1 an embodiment of the invention.
Figure 2:
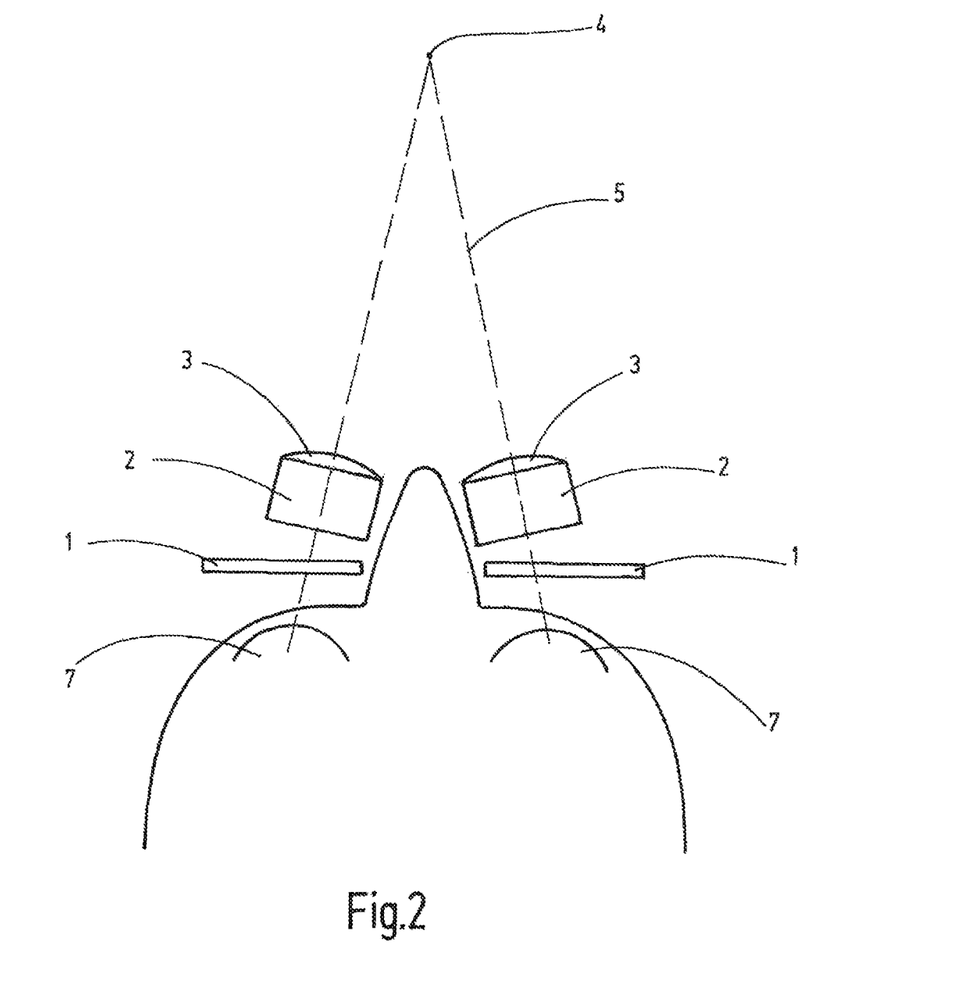
FIG. 2 the embodiment of FIG. 1 in a view from above.
Figure 3:
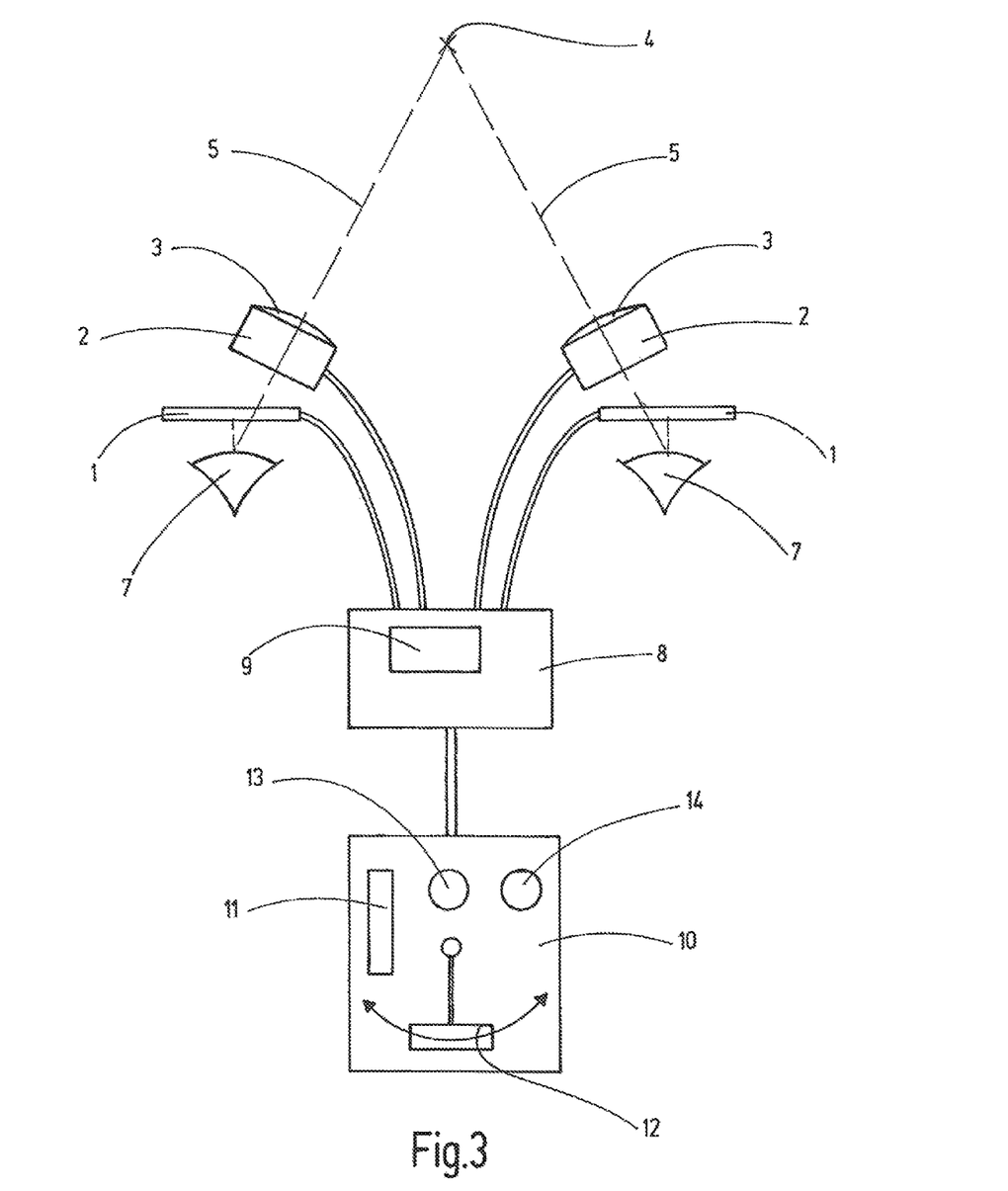
FIG. 3 the view from above as well as other elements of the embodiment.

FIG. 1 shows a first exemplary embodiment of the invention in a lateral view. FIG. 2 shows the embodiment of FIG. 1 in a view from above. FIG. 3 shows the view from above as well as additional elements of the embodiment.

A device for obtaining and processing of 3D images, for example in the form of an optical 3D scanner, includes a head assembly 6. The head assembly 6 is a device with which the device can be mounted on the head of a user so that the device is fixed relative to the head. The head assembly 6 can be constructed in the shape of a helmet, a hat, a bonnet or a cap. Feasible is also a head assembly 6 in the form of a headphone that is placed on the head or the ears, or eyeglasses held by elements resting on the nose and the ears.

The head assembly 6 includes two cameras 2 and two displays (monitors) 1. Both cameras 2 and both displays 1 can be attached to the "head assembly" 6. The head assembly 6 can be customized to the user, especially his eyes 7, so that the optical axes of the monitors 1 coincide with the optical axes of the eyes 7 of the user of the device. Both camera systems 2 are focused to a common focal point 4. The distance of the focal point 4 can be varied with the device. The cameras 2 can are also enlarge the object by way of the zoom function of the camera systems 2 (digital zoom) and/or the employed optics 3 (optical zoom). A foot switch 10 is connected to a computer 8, by which the focus 11 and the magnification 12 can be controlled. The computer 8 also includes foot switches for the image-acquisition function 13 and/or the video function 14. Since the distance 5 between the two cameras 2 and their focal point 4 is known, the object can be measured and/or or captured in three dimensions. In addition, position sensors 15 can be mounted on the head assembly to detect the position of the head assembly 6. These position data can be reconciled with other position sensor data to determine a relative position.

An exemplary industrial application of the invention is in dentistry. For example, the invention can be used as VR microscope eyepieces. In this case, the reality is recorded with the cameras in real time and displayed on the monitors. The magnified image can be viewed with the zoom function. Magnifications of up to 10 times are possible, without excessively blurring the picture.

Treatments from the perspective of the practitioner can be documented by enabling video recording. Furthermore, this function can also be used for training purposes by enabling live transmission or recording videos.

The practitioner can be provided with outside information by superimposing information on the live image. For example, the required placement and length of a cut can be displayed. Furthermore, an outsider can see when a scalpel is not placed in accordance with the cut, and can then take corrective action. A miscut can thereby be more easily prevented.

An instructor may also switch his VR microscope eyeglasses to the VR-microscope eyeglasses of his trainees or students and then see what each trainee sees. An instructor can then be in several places at the same time. It does not matter where the instructor is located, as long as the video signal is available to him in real-time or in near real-time.

Figure 4:
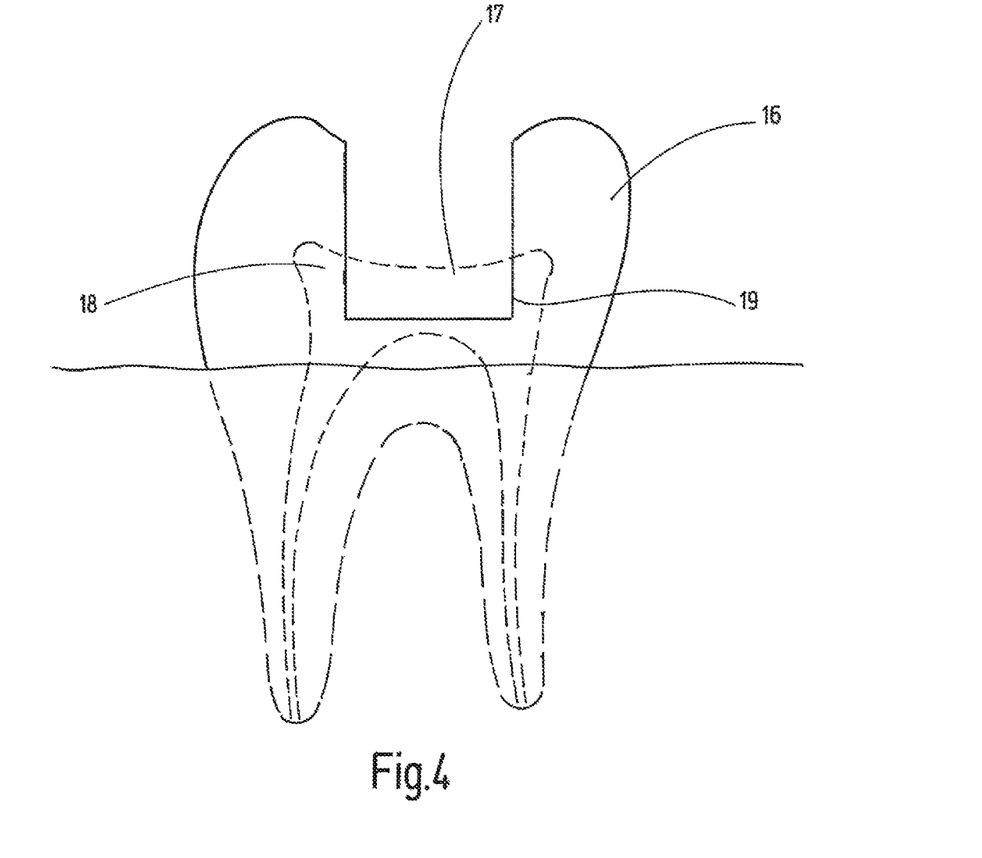

FIG. 4 shows in exemplary and schematic form a 3D X-ray image superimposed on a 3D tooth image during a root canal procedure. The 3D X-ray image 17 is superimposed on the real tooth 16. Root canals 18 and entrances 19 of the root canals 18 located in the tooth are displayed. The image of 3D tooth image with the superimposed 3D X-ray image can be zoomed, so that the entrances 19 can be more easily found. The root can be superimposed on the image of the real tooth.

Figure 5:
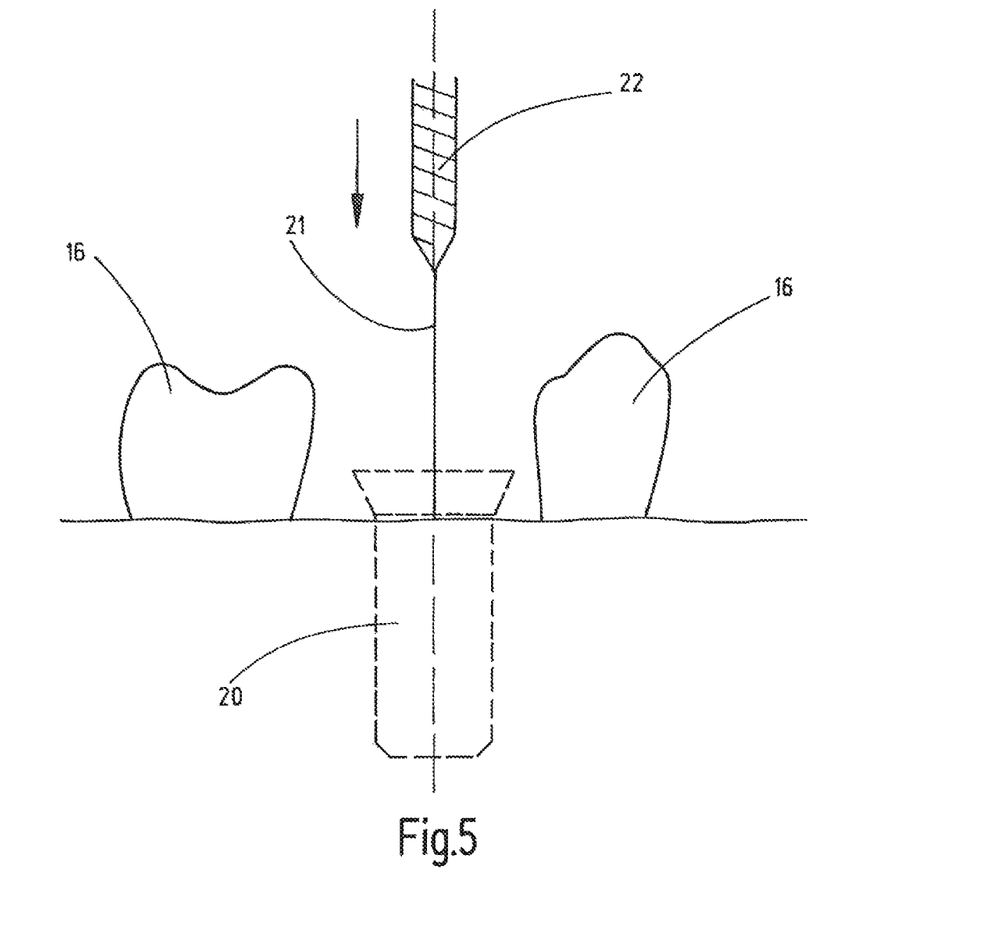
Figure 6:
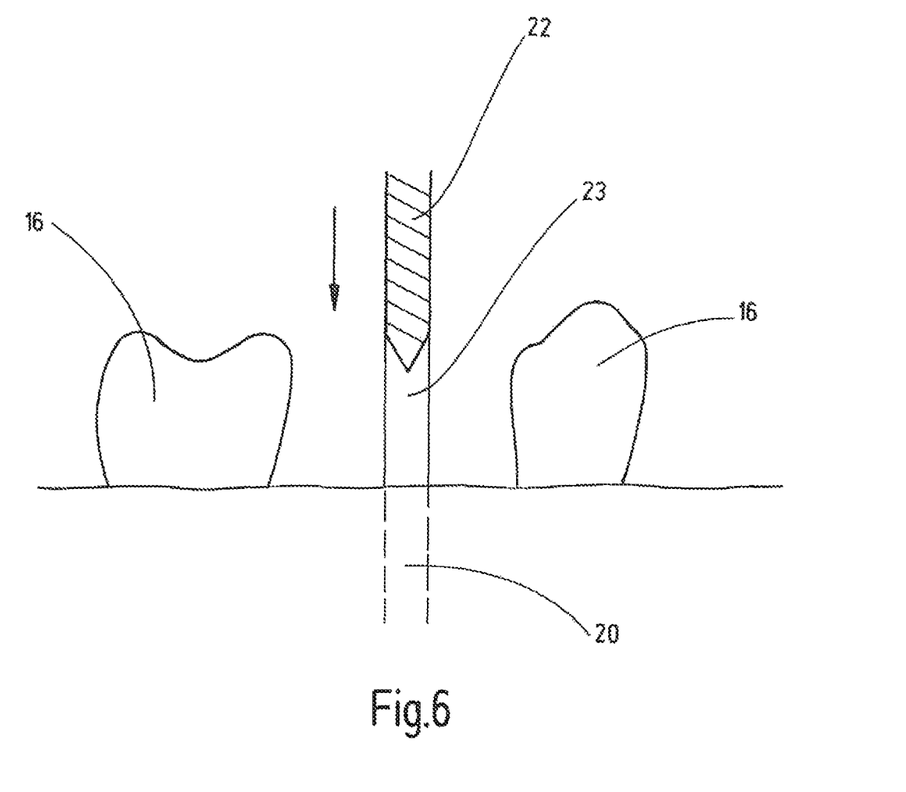
Figure 7:
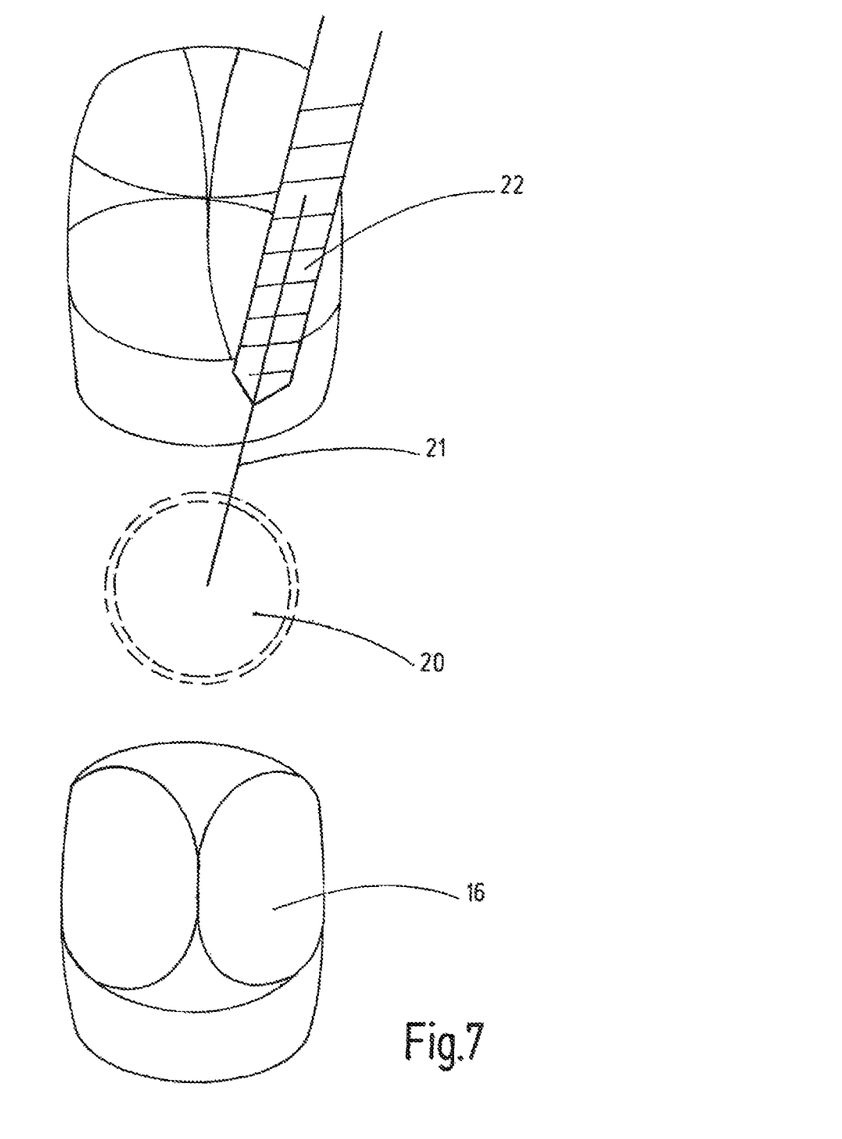

FIGS. 5 to 7 show in exemplary and schematic form 3D X-ray images with superimposed 3D tooth images as part of an implant. The implant planning 20 is included when superimposing the 3D X-ray images on the real situation. The user thus virtually sees the implant 20 between the real teeth 16. The implant axis 21 is displayed as an extension of the implant. The user can then readily position an implant drill axis 22 so as to coincide with the implant axis 21 for placing the drill hole necessary for the implant with the correct direction and at the correct position. By using implant planning software, the implant drills to be used can be virtually and incrementally displayed with the appropriate spatial orientation, so that when actually drilling the real drill must only be overlaid with the virtually displayed drill 23. However, for these and other applications, the position of the VR eyeglasses and the position of the patient must be known, as well as the superposition of the patient and the 3D X-ray image. This can be accomplished using the position sensors 15. In addition or as an alternative to the position sensors, markers, for example balls or bodies with optical patterns, via which the position of the model carrier can be calculated, may also be attached to the model base.

Vulnerable regions, such as nerves or large vessels, may be displayed during surgical procedures. The necessary information can come from a previously made diagnosis or from a model.

When placing fillings, the surface of a new filling of the ground tooth can be calculated by using a 3-D impression of the ground tooth based on so-called tooth databases. This surface may be transparently overlaid. By modelling the filling, surfaces that are modeled as being too high, as well as surfaces that are modeled as being too low, can be coded. This can also be done in conjunction with simultaneous magnification, wherein sensitive areas in the tooth, for example the nerve, can additionally be displayed by using 3D X-ray images.

Figure 8:
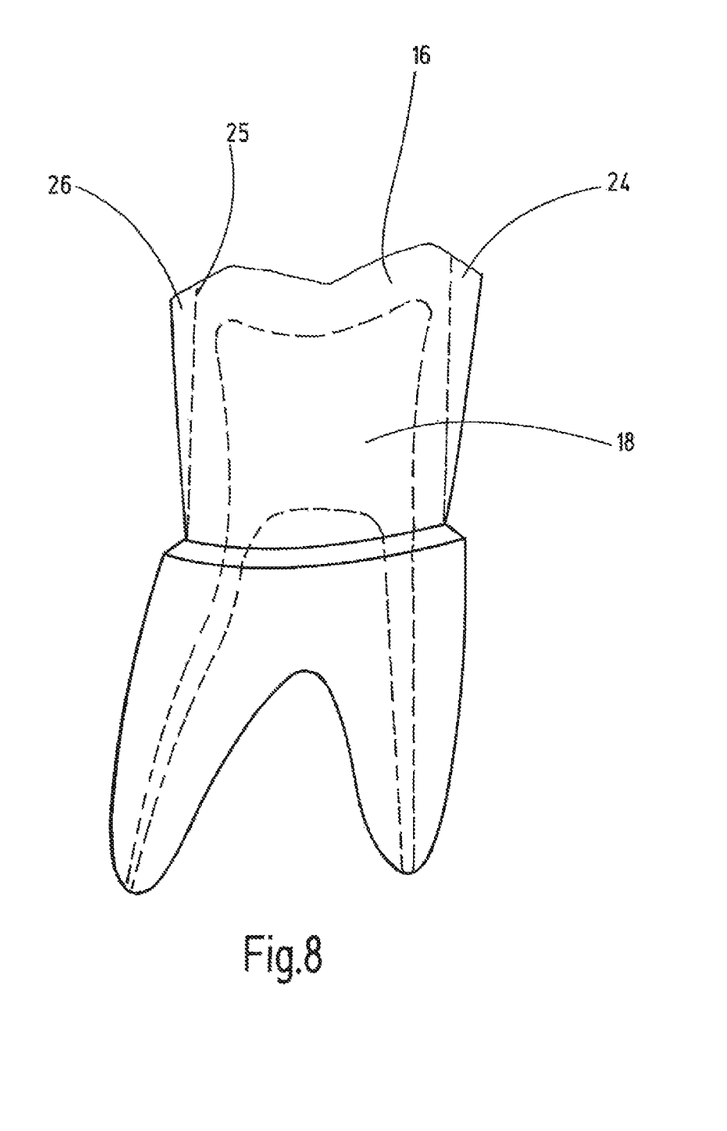

FIG. 8 shows in exemplary and schematic form a 3D tooth image overlaid with 3D X-ray image in conjunction with grinding (preparing) of a tooth. When grinding the tooth 16 for a crown/bridge or a partial crown 24, the optimal material removal of tooth structure can be displayed after entering the subsequently used material. This allows, on the one hand, working gently with minimum damage to the tooth substance and, on the other hand, removing sufficient material to ensure material-dependent stability. Again, color coding 26 may also be used here. Data from 3D X-ray images can still be used to superimpose the tooth nerve 18. It can be checked and displayed visually, whether teeth were ground down parallel without undercuts 25 for subsequently placing a crown/bridge on the teeth.

Figure 9:
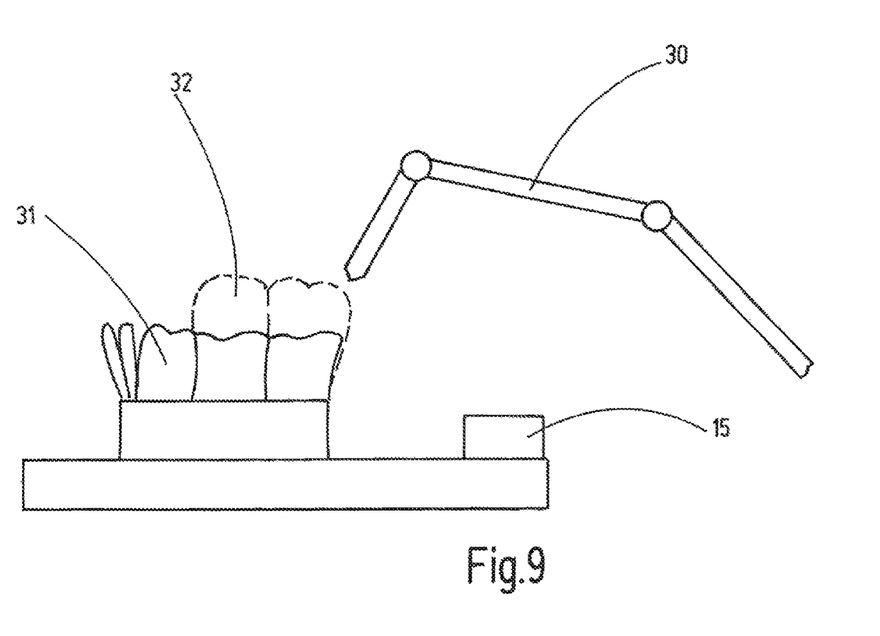

FIG. 9 shows in exemplary and schematic form a 3D X-ray image overlaid with a 3D tooth image in the context of dentistry. In conjunction with haptic feedback instruments 30, dental prostheses can be virtually constructed on the model of the patient 31 and the construction 32 can be virtually superimposed on the real model. The dental technician can rotate and turn the model in all directions by using the position sensors 15, wherein the correct view of the virtual modeling 32 is always displayed on the real model 31. Additionally or alternatively to the location sensors, markers, for example balls or bodies with optical patterns, via which the position of the model carrier can be calculated, may also be attached to the model base. The sensors can be connected to the computer 8 via a wired and/or wireless link, for example via a radio link. Of course, the view can also be magnified in this case. Tooth databases can also be displayed, with color coding. Additional information about the function, for example the movements of the lower jaw, can be displayed as superposition. For example, areas of the tooth, which can interfere with movements of the lower jaw, may be displayed and again color coded.

It is also possible to use the VR microscope eyepieces as a 3D camera for recording ground teeth to create an optical impression. Due to the possible magnification, the crown margin can be much more accurately optically detected and displayed. The thus recorded images or video sequences can be converted into the STL data format, allowing the data to be processed with any commercially available CAD/CAM program.

In an exemplary embodiment, the microscope eyepieces are technically distinguished also by the fact that the distance between the eyes of the displays is adjustable. The distance between the two camera systems can also be variably adjusted so that the user can adjust them commensurate with the distance between his eyes.

The two-camera systems may, but need not necessarily be electrically synchronized with each other.

The optical axes of the camera systems are aligned relative to each other such that they are horizontally either parallel to each other or angled relative to each other, so that they have a common focal point located in front of the system at the distance 5 between, for example, fifteen (15) cm and infinity. In the vertical direction, the optical axis is either horizontal or inclined downward up to an angle of 80°.

Figure 10:
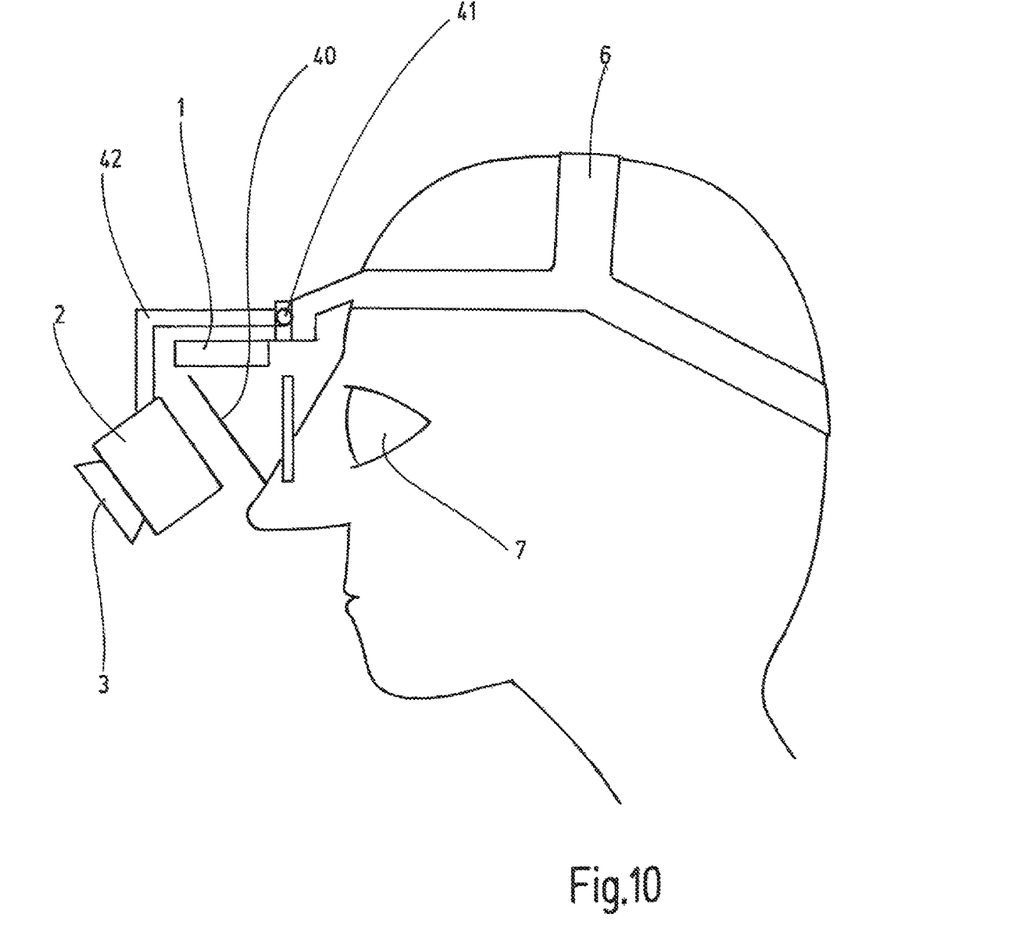
FIG. 10 another embodiment of the invention.

In another exemplary embodiment of the invention, the system may be constructed so that semi-transparent optical glasses, onto which the camera images can be projected, can be used instead of two displays. This is schematically shown in FIG. 10. No increase in magnification is here available in the basic mode because in the absence any technical visual system the user sees only with his own eyes 7 through the transparent glasses 40 (similar to a pair of sunglasses). Virtual information can then be projected on the transparent glasses 40. A correct overlay of information will only work if the projected information has the same size as the viewed object. The head assembly 6 has an arm 42 which can rotate about a pivot point 41 and on which the camera 2 is arranged.

When the microscope mode is switched on, i.e. the information is displayed with magnification, the semi-transparent optical glass 40 is automatically completely darkened, and the image of the camera system in conjunction with the virtual information is displayed or projected onto the now completely opaque glasses 40. In these glasses, the camera system 2 cannot be mounted to coincide with the optical axis of the eye, but instead either on the side or above or below the eye. Otherwise, the same rules as described previously apply to the camera system.

Figure 11:
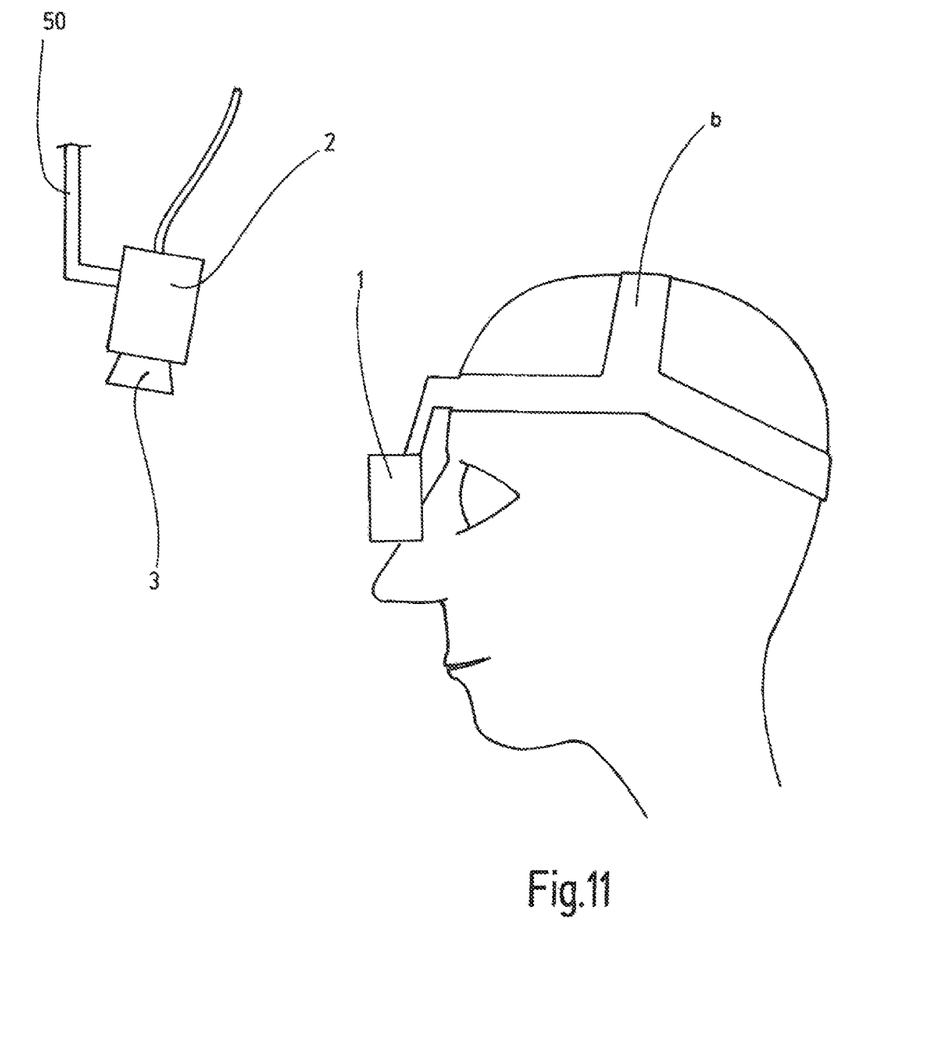
FIG. 11 yet another embodiment of the invention.

A yet another exemplary embodiment of the invention, which is illustrated schematically in FIG. 11, contemplates separating of the optical systems. In this case, the optical recording system 2 is spatially separated from the display system 1. In this example, the optical recording system 2 may be attached at the OP lamp or a tripod 50, with the information being displayed in the display system 1. Here, the display system can be modified such that the eye movement and viewing direction is detected by corresponding sensors, with the optical recording system adapting accordingly. The adaptation includes the alignment of the optical axes of the two camera systems and the location of the focal point.

These are merely several examples of applications in dentistry and dental technology. Many applications or procedures in other fields of medicine as well as in the production are similar. A device according to the invention can also be implemented as part of a closed helmet, for example for applications in fire departments or for military applications. A closed helmet offers the wearer greater safety, with the use of cameras allowing additional functions. A not exhaustive list of functional capabilities includes: zooming and magnified vision, displaying building plans and the own position inside the building, displaying colleagues, potential use of color filters and infrared displays.

The invention claimed is:

1. A device for capturing and processing of three-dimensional (3D) images, comprising:
   a head assembly wearable by a user,
   two cameras arranged on the head assembly and synchronized with each other so that the cameras focus to a common focal point with identical aperture and identical zoom, wherein one of the cameras is a guide camera selected by the user to guide synchronization and the two cameras are designed for magnification,
   a monitor associated with each camera and configured to display a corresponding camera image of the each camera, wherein the monitors are mounted on the head assembly which is customizable such that optical axes of the monitors coincide with optical axes of the eyes of the user,
   a data processing unit is configured for processing image data of the camera images from each camera; and
   a foot switch connected to the data processing unit, wherein at least one of the focus and the magnification of the two cameras is controllable by the foot switch,
   wherein
     the data processing unit superimposes, on the camera images, digital information,
     the digital information is, at least partially, imported from an implant planning tool and the data processing unit superimposes, on the camera images, a rendering of a virtual implant, and
     the rendering of the virtual implant comprises a visualization of an implant axis as an extension of the virtual implant.

2. The device of claim 1, wherein the digital information comprises 3D X-ray images of a tooth.

3. The device of claim 2, wherein the 3D X-ray images are images of root canals, tooth roots, nerves or blood vessels, or a combination thereof.

4. The device of claim 1, wherein the data processing unit superimposes on the camera images a surface of a new filling.

5. The device of claim 4, wherein a partial area of the surface having a height that is different from a desired height is displayed color-coded.

6. The device of claim 1, further comprising at least one haptic feedback instrument designed to construct a virtual model.

7. The device of claim 1, wherein the device is designed to record an optical 3D impression of a ground tooth and wherein the optical 3D impression is then supplied to a system for computer-aided modeling and/or computer-aided manufacturing.

* * * * *